United States Patent [19]

James et al.

[11] 4,141,363

[45] Feb. 27, 1979

[54] INTERLOCKING SUTURE

[76] Inventors: Jesse L. James; George Spector, both c/o George Spector, 3615 Woolworth Bldg., 233 Broadway, New York, N.Y. 10007

[21] Appl. No.: 633,849

[22] Filed: Nov. 20, 1975

[51] Int. Cl.² .............................................. A61B 17/04
[52] U.S. Cl. .................................................... 128/335
[58] Field of Search ............ 128/334 R, 335, 155-157, 128/169

[56] References Cited

U.S. PATENT DOCUMENTS

| 1,969,188 | 8/1934 | Spicer | 128/335 |
| 2,798,492 | 7/1957 | Barnes et al. | 128/335 |
| 2,818,865 | 1/1958 | Jacoby | 128/334 R |
| 2,891,546 | 6/1959 | Galloway | 128/295 |
| 3,402,716 | 9/1969 | Baxter | 128/335 |

FOREIGN PATENT DOCUMENTS 831401  3/1960  United Kingdom ..................... 128/335

*Primary Examiner*—Dalton L. Truluck

[57] ABSTRACT

A special type of suture tape for use in the medical field, and which holds a wound or laceration edges together for mending and healing; the device consisting of a pair of interlocking suture tapes, each of which has one end applied to the skin on each opposite side of the wound, the opposite ends of the tapes then being pulled in opposite directions so to draw the wound edges together so to close the wound, after which the other ends of the crossing tapes are pressed down against the skin, thus keeping the wound closed.

1 Claim, 6 Drawing Figures

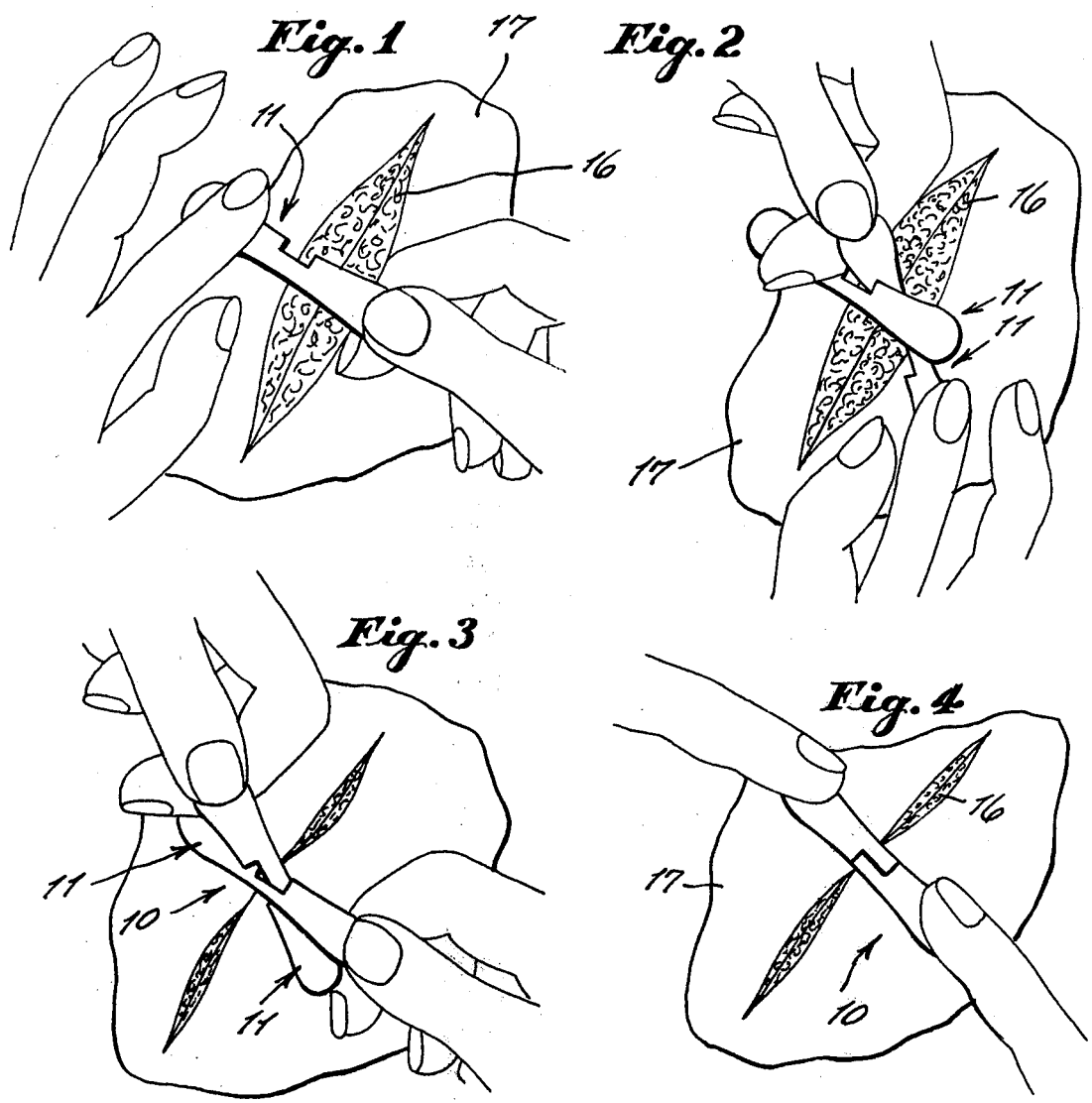
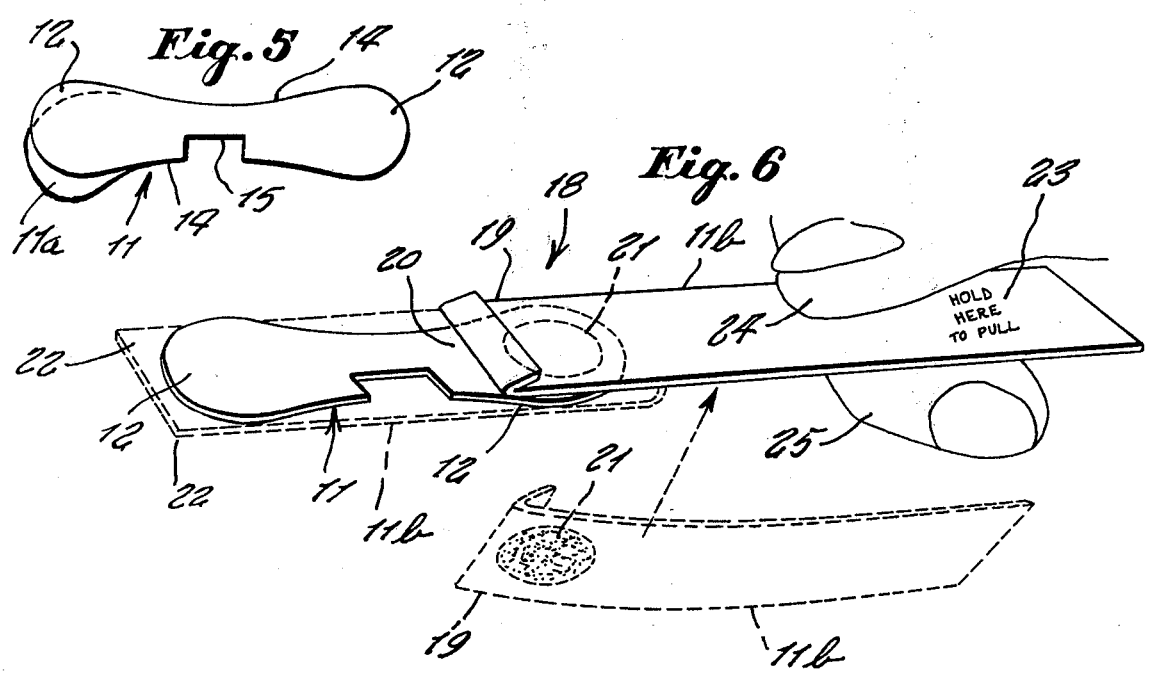

4,141,363

INTERLOCKING SUTURE

This invention relates generally to bandage tapes such as are sued in dressing a wound. More specifically, it relates to suture tapes.

A principle object of the present invention is to provide an improved, interlocking suture which serves to first draw the opposite side edges of a wound or laceration together so to close the same, and then serves to retain the same in the closed position during the healing time, thus being an improvement over conventional existing suture tapes which require a separate prior step by other means to first close a wound before the tapes are applied, for the sole purpose of only retaining the wound in the already closed position.

Another object is to provide an interlocking suture which is quick and easy to apply without any special skill so that would be ideal to be included in any first aid kit.

Other objects are to provide an interlocking suture having the advantages of (1) fast closing of a wound (2) leaving no unsightly scars resulting from needle punctures of a conventional suturing, (3) not being painful nor difficult to remove the suture after a healing of a wound, such as in the case of needle and thread type sutures, (4) being more applicable in emergency cases where the unavailability of proper lighting would rule out suturing by a needle and thread, (5) no need for anesthetizing a patient or numbing of injured area so to close the wound, such as is necessary in most cases where suturing is done by a needle and thread, and (6) there being no further injury to the skin around a wound, as is sometimes the case when suturing with a needle, and in attempt to close a wound tightly, the needle and thread sutures are placed as close as possible to the edge of the wound so that sometimes the needle tears the skin from the penetration point out to the edge of the wound.

Still other objects are to provide an interlocking suture which is simple in design, inexpensive to manufacture, rugged in construction, easy to use and efficient in operation.

These and other objects will be readily evident upon a study of the following specification and the accompanying drawing wherein:

FIGS. 1 through 4 show subsequent steps in applying the present invention across a wound.

FIG. 5 is a plan view of one of the invention components shown with cover paper being peeled off.

FIG. 6 is a perspective view of a modified design of the invention which includes a novel protective paper to cover the adhesive and which when partly pulled off serves as a convenient handle while working with the suture so to prevent fingers touching the adhesive which would depreciate the adhesive holding qualities thereof.

Referring now to the drawing in detail, and more particularly to FIGS. 1 through 5 thereof, the reference numeral 10 represents an interlocking suture according to the present invention wherein there are a pair of interlocking bandage tapes 11 both of which are a same size and shape. Each tape is of elongated character, die-cut from a thin, flexible, plastic or fabric sheet having pressure sensitive adhesive applied to one entire side thereof, after which the adhesive is covered temporarily, prior to use, by a glossy cover paper 11a that can be peeled off. Each tape has widened, rounded opposite ends 12 while the longitudinal intermediate portion 13 therebetween is narrowed in width due to inwardly bowed opposite side edges 14. Additionally a rectangular cut out section or notch 15 is cut out at a longitudinal center of one of the side edges 14; the depth of the notch being one half of the width of the intermediate portion 13.

Both of the tapes being the same, accordingly one can be turned 180° so that, in use, the notches can be interfitted, as shown in FIG. 3.

In operative use, to close a wound 16, the two tapes are applied to the skin 17 on opposite sides of the wound, in the subsequent steps that are illustrated in FIGS. 1 through 4 of the drawings and as is described herebelow:

FIG. 1. The first special interlocking suture tape is applied to one side of the wound. (Please note that in the center of the length of the butterfly suture tape there is a cutout section.) The one end of the interlocking suture tape is pressed to the skin getting a firm adhereing seal.

FIG. 2. A second special interlocking suture tape is applied to the opposite side of the wound with the cutout section facing the cutout section of the first tape. The one end of the second tape is pressed firmly to the skin making a solid seal as was the first tape on the opposite side of the wound.

FIG. 3. The loose ends of each special interlocking suture tape are gripped with the fingers, interlocking the cutout sections of each suture and then, by pulling the loose ends of the sutures crisscross over the wound in opposite directions, the edges of the wound are drawn together.

FIG. 4. When the edges of the wound are drawn together, the loose ends of both special interlocking suture tapes are pressed down on their opposite sides of the wound thus stabilizing the closure of the wound.

Referring now to FIG. 6, a modified design 18 of the invention includes the above described two tapes 11, however, the cover paper 11a is substituted by a cover paper 11b that is longer on one end 19 and folded over the top side 20 of the tape and secured thereto by a spot 21 of pressure sensitive adhesive applied to the adjacent end 12. The paper 11b is of rectangular shape so to form pull tabs 22 at its other end for easy grasp so to peel off the tape.

In operative use, when the paper 11b is peeled off the adhesive that covers the entire one side of the tape, it still remains attached to the tape by the spot 21 so that the paper forms a long handle for being grasped, where indicated by text 23, between fingers 24 and 25 so to prevent them touching the adhesive surface and spoiling its full adhesive efficiency.

These special interlocking sutures can be used in multiples for the closure of any wound that is not too great in depth or length, or which does not require internal sutures.

While various changes may be made in the detail construction, it is understood that such changes will be within the spirit and scope of the present invention as is defined by the appended claims:

What is claimed is:

1. An interlocking tape suture, comprising a flexible, thin material having pressure sensitive adhesive applied on one entire side thereof and covered by a glossy paper that is peelable away from said adhesive, said tape being of elongated shape having similar wider, rounded opposite ends and a tapering narrower width longitudinal central portion formed by inwardly tapering opposite longitudinal spaced side edges, wherein one said side edge having a rectangular notch at said center, the depth of said notch being one-half the width of said narrower longitudinal central portion, wherein said peelable glossy paper is substantially longer than said tape on one end, said longer end of said paper being folded over around an opposite side of an adjacent end of said tape, and secured there to wherein said glossy paper includes extending tab portions on its opposite end so to be readily grasped for being peeled from said tape and wherein a small spot of pressure sensitive adhesive is applied upon said tape opposite side adjacent end, and said folded over glossy paper end being engaged by said adhesive spot.

* * * * *